US007230055B2

(12) United States Patent
Musa

(10) Patent No.: US 7,230,055 B2
(45) Date of Patent: Jun. 12, 2007

(54) COMPOSITIONS CONTAINING OXETANE COMPOUNDS FOR USE IN SEMICONDUCTOR PACKAGING

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 461 days.

(21) Appl. No.: 10/901,631

(22) Filed: Jul. 29, 2004

(65) Prior Publication Data

US 2006/0025542 A1   Feb. 2, 2006

(51) Int. Cl.
C07D 305/04      (2006.01)
C07D 305/06      (2006.01)
C08L 63/00       (2006.01)
C08L 67/00       (2006.01)
C08L 77/00       (2006.01)

(52) U.S. Cl. ............... 525/410; 525/186; 525/422; 549/510

(58) Field of Classification Search ............... None
See application file for complete search history.

(56) References Cited

U.S. PATENT DOCUMENTS

| 3,278,554 | A | | 10/1966 | Stark | |
| 3,577,438 | A | | 5/1971 | Melaas | |
| 4,225,691 | A | | 9/1980 | Crivello | |
| 6,117,944 | A | * | 9/2000 | Nishikubo et al. | 525/109 |
| 6,498,200 | B1 | * | 12/2002 | Suzuki et al. | 522/13 |
| 6,586,496 | B1 | * | 7/2003 | Takamatsu et al. | 522/168 |
| 6,753,434 | B1 | * | 6/2004 | Musa | 549/510 |
| 6,953,862 | B2 | * | 10/2005 | Musa | 549/510 |
| 6,982,338 | B2 | * | 1/2006 | Musa | 548/517 |
| 7,034,064 | B2 | * | 4/2006 | Musa | 522/181 |
| 7,057,063 | B2 | * | 6/2006 | Nishikubo et al. | 560/90 |
| 2002/0089067 | A1 | | 7/2002 | Crane et al. | |
| 2002/0143112 | A1 | | 10/2002 | Weinert et al. | |
| 2004/0155364 | A1 | * | 8/2004 | Doba | 257/789 |
| 2005/0267254 | A1 | * | 12/2005 | Mizori et al. | 524/589 |

FOREIGN PATENT DOCUMENTS

| JP | 11-246541 | A | * | 9/1999 |
| JP | 11-269370 | A | * | 10/1999 |
| JP | 11-315181 | A | * | 11/1999 |
| JP | 11-343346 | A | * | 12/1999 |
| JP | 2001-40205 | A | * | 2/2001 |
| JP | 2001-329112 | A | * | 11/2001 |
| JP | 2001329112 | | | 11/2001 |
| JP | 2003-160729 | A | * | 6/2003 |
| WO | WO 02/06038 02 | | | 1/2002 |
| WO | WO 02/06038 03 | | | 1/2002 |
| WO | WO 02/28985 | | | 4/2002 |
| WO | WO 2004/101541 | | | 11/2004 |

OTHER PUBLICATIONS

Sato et al., Journal of Polymer Science: Part A: Polymer Chemistry, vol. 39, 2001, pp. 1269-1279.*
CAPLUS accession No. 1963:455552 for Campbell et al., Journal of Polymer Science: Part A 1, 1963, two pages.*
CAPLUS accession No. 2003:771940 for Komatsu et al., Nettowaku Porima, vol. 43, No. 3, 2003, two pages.*
Ledwith, Anthony: "Possibilities for promoting cationic polymerization by common sources of free radicals"; *Polymer 1978*, vol. 19; October; pp. 1217-1222.
Sasaki, Hiroshi et al.: "Photoinitiated Cationic Polymerization of Oxetane Formulated with Oxirane"; *Journal of Polymer Science Part A*; vol. 33; 1995; pp. 1807-1816.
Searles, Scott et al.: "Hydrogen Bonding Ability and Structure of Ethylene Oxides"; *This Journal*;73;3704;1951.
Xianming, Hu et al.: "Phase-Transfer Synthesis of Optically Pure Oxetanes Obtained from 1,2,2-Trisubstituted 1,3-Propanediols"; *Synthesis May 1995*; pp. 533-538.
Fujiwara, Tomoko et al.: "Synthesis and Characterization of Novel Oxetane Macromonomers"; *Polymer Preprints 2003*; 44(1), 785.
Dhavalikar, R. et al.: "Molecular and Structural Analysis of a Triepoxide-Modified Poly(ethylene terephthalate) from Rheological Data"; *Journal of Polymer Science*: Part A: Polymer Chemistry; vol. 41, 958-969 (2003); pp. 958-969.
Satoh, Toshifumi et al.: "A Novel Ladder Polymer. Two-Step Polymerization of Oxetanyl Oxirane Leading to a "Fused 15-Crown-4 Polymer" Having a High $Li^+$-Binding Ability"; *Macromolecules 2003*, 36, 1522-1525.
Chen, Yu et al.: "Synthesis of Multihydroxyl Branched Polyethers by Cationic Copolymerization of 3,3-Bis(hydroxymethyl)oxetane and 3-Ethyl-3-(hydroxymethyl)oxetane"; *Journal of Polymer Science*: Part A: Polymer Chemistry, vol. 40, 1991-2002; 2002 Wiley Periodicals, Inc.
Nishimura, Tomonari et al.: "Chemoselective isomerization of amide-substituted oxetanes with Lewis acid to give oxazine derivatives or bicyclic amide acetals"; *Chem. Commun.*, 1998; pp. 43-44.
Miwa, Yoshiyuki et al.: "Polymerization of Bis-Oxetanes Consisting of Oligo-Ethylene Oxide Chain with Lithium Salts as Initiators"; *Polym. J.*, vol. 33, No. 8, 2001; pp. 568-574.
Ichikawa, Eiko et al.: "Synthesis of Oxetanocin A and Related Unusual Nucleosides with Bis(hydroxymethyl)-branched Sugars"; *Synthesis 2002*, No. 1, Dec. 28, 2001; Georg Thieme Verlag Stuttgart, NY; pp. 1-28.

(Continued)

Primary Examiner—Robert Sellers
(74) Attorney, Agent, or Firm—Jane E. Gennaro

(57) ABSTRACT

Compositions containing oxetane compounds having ester, amide, urea, carbamate, carbonate, or carbonyl functionality one carbon atom removed from the oxetane ring cure at high temperatures are suitable for use as underfill materials within a semiconductor package, particularly in applications using lead free solder electrical interconnections. A suitable oxetane compound has the structure:

3 Claims, 4 Drawing Sheets

OTHER PUBLICATIONS

Minegishi, Shouji et al.: "Synthesis of Polyphosphonates Containing Pendant Chloromethyl Groups by the Polyaddition of Bis(oxetanes)s with Phosphonic Dichlorides"; *Journal of Polymer Science*: Part A: Polymer Chemistry, vol. 40 3835-3846; 2002 Wiley Periodicals, Inc.

Sasaki, Hiroshi et al.: "Photoinitiated Cationic Polymerization of Oxetane Formulated with Oxirane"; *Journal of Polymer Science*: Part A: Polymer Chemistry, vol. 33, 1807-1816; 1995 John Wiley & Sons, Inc.

Rosenbaum, DR. Barry et al.: "Develop Better Coatings"; *OMNOVA Solutions Inc.*, Akron, OH; pp. 1-5.

Sasaki, Hiroshi: "Application of Oxetane Monomers for UV-Curable Materials"; RadTech 2002; Tech. Conf. Proceedings; pp. 64-78.

Carter, Wells et al.: "New Oxetane Derivative Reactive Filuent for Cationic UV Cure"; *RadTech 2000*; Tech. Proceed.; pp. 641-649.

Crivello, J. V. et al.: "Diaryliodonium Salts as Thermal Initiators of Cationic Polymerization"; *Journal of Polymer Science*: Polymer Chemistry Ed, vol. 21, 97-109 (1983); John Wiley & Sons, Inc.

Lu, Yong-Hong et al.: "Synthesis of Side-Chain Liquid Crystalline Polyoxetanes Containing 4-(Alkanyloxy)phenyl *trans*-4-Alkylcyclohexanoate Side Groups"; *1995 American Chem. Society*; pp. 1673-1680.

Lu, Yong-Hong et al.: "Synthesis of side-chain liquid crystalline polyoxetanes containing 4-dodecanyloxphenyl *trans*-4-alkylcyclohexanoate side groups"; *Polymer Bulletin 32*, 551-558 (1994); Springer Verlag.

Hsu, Li-Ling et al.: "Studies on the Synthesis and Properties of Ferroelectric Side Chain Liquid Crystalline Polyoxetanes"; *Journal of Polymer Science*: Part A: Polymer Chemistry; vol. 35, 2843-2855; (1997); John Wiley & Sons, Inc.

Kawakami, Yusuke et al.: "Synthesis and Thermal Transition of Side-chain Liquid Crystalline Polyoxetanes Having Laterally Attached Mesogenic Group"; *Polymer International*; 0959-8103/93; Great Britain.

Kawakami, Yusuke et al.: "Synthesis of Liquid Crystalline Polymers with a Polyoxetane Main Chain"; *Macromolecules*; vol. 24, No. 16, 1991; pp. 4531-4537.

Kawakami, Yusuke et al.: "Smectic liquid crystalline polyoxetane with novel mesogenic group"; *Polymer Bulletin 25*; Springer-Verlag 1991; pp. 439-442.

Crivello, J.V. et al.: "Photoinitiated Cationic Polymerization With Multifunctional Vinyl Ether Monomers"; *Journal of Radiation Curing*, Jan. 1983; pp. 6-13.

Ishizone, Takashi et al.: "Protection and Polymerization of Functional Monomers. 29. Syntheses of Well-Defined Poly[(4-vinylphenyl)acetic acid], Poly[3-(4-vinylphenyl)propionic acid], and Poly(3-vinylbenzoic acid) by Means of Anionic Living Polymerizations of Protected Monomers Bearing Bicyclic Ortho Ester Moieties"; *Macromolecules 1999*, 32, 1453-1462.

Sato, Kazuya et al.: "New Reactive Polymer Carrying a Pendant Oxetane Ring"; *Macromolecules 1992*, 25, 1198-1199; Communications to the Editor.

Moussa, K. et al.: "Light-Induced Polymerization of New Highly Reactive Acrylic Monomers"; *Journal of Polymer Science*: Part A: Polymer Chemistry, vol. 31, 2197-2203 (1993); John Wiley & Sons, Inc.

Kawakami, Yusuke et al.: "Synthesis of Liquid Crystalline Polyoxetanes Bearing Cyanobiphenyl Mesogen and Siloxane-Containing Substituent in the Repeating Unit"; *Polymer Journal*, vol. 28, No. 10, pp. 845-850 (1996).

Crivello, J.V. et al.: "Synthesis and Photopolymerization of Silicon-Containing Multifunctional Oxetane Monomers"; *J.M.S.-Pure Appl. Chem.*, A30(2 & 3), pp. 173-187 (1993); Marcel Dekker, Inc.

Chappelow, C. C. et al.: "Photoreactivity of Vinyl Ether/Oxirane-Based Resin Systems"; *Journal of Applied Polymer Science*, vol. 86, 314-326 (2002); Wiley Periodicals, Inc.

Toagosei Co. Ltd.: "Developing Monomers".

"Oxetane"; Copyright 2000 American Chemical Society.

Hou, Jian et al.: "Synthesis of a Star-Shaped Copolymer with a Hyperbranched Poly(3-methyl-3-oxetanemethanol) Core and Tetrahydrofuran Arms by One-Pot Copolymerization"; *Macromol. Rapid Commun.* 2002, 23, 456-459.

Xu, Jun et al.: "Study On Cationic Ring-Opening Polymerization Mechanism of 3-Ethyl-3-Hydroxymethyl Oxetane"; *J. Macromol. Sci.-Pure App. Chem.*, A39(5), 431-445 (2002); Marcel Dekker, Inc.

Suzuki, Hiroshi et al.: "Photo-cationic curable materials using cationic polymerizable monomers such as epoxides and vinyl ether derivatives"; *Polymer Preprints 2001*, 42(2), 733.

Kanoh, Shigeyoshi et al.: "Monomer-Isomerization Polymerization of 3-Methyl-3-(phthalimidomethyl)oxetane with Two Different Ring-Opening Courses"; *Macromolecules 1999*, 32, 2438-2448; 1999 American Chemical Society.

Jansen, Johan F.G.A. et al.: "Effect of Dipole Moment on the Maximum Rate of Photoinitiated Acrylate Polymerizations"; *Macromolecules 2002*, 35, 7529-7531; 2002 American Chemical Society; Communications to the Editor.

Crivello, J. V. et al.: "Structure And Reactivity Relationships In The Photoinitiated Cationic Polymerization Of Oxetane Monomers"; *J.M.S.-Pure Appl. Chem.*, A30(2&3), pp. 189-206 (1993); Marcel Dekker, Inc.

Machida, Shigeru et al.: "The Highly *Syn*-Selective Michael Reaction Of Enamines With 2-(1-Alkenyl)-1,3-Dioxolan-2-Ylium Cations Generated From 2,2-Dimethoxyethyl 2-Alkenoates In Situ"; *Tetrahedron* vol. 47, No. 23, pp. 3737-3752, 1991; 1991 Pergamon Press plc.

Motoi, Masatoshi et al.: "Preparation of Polyoxetane-Polystyrene Composite Resins and Their Use as Polymeric Supports of Phase-Transfer Catalysts"; *Polymer Journal*, vol. 21, No. 12, pp. 987-1001 (1989).

Pattison, Dexter B.: "Cyclic Ethers Made by Pyrolysis of Carbonate Esters"; *Orchem Laboratories* E.I. DuPont; Jan. 17, 1957.

Smith, Tara J. et al.: "Ring Opening of 2-Ethyl-2-Hydroxymethyl Oxetane Under Basic Conditions"; *Polymer Preprints 2002*, 43(2), 984.

Nishikubo, Tadatomi et al.: "Synthesis of Alternating Copolyesters of Oxetanes With Cyclic Carboxylic Anhydrides Using Quaternary Onium Salts"; *Polymer Preprints 2002*, 43(2), 1135-1136.

Amass, A. J. et al.: "Studies In Ring-Opening Polymerization-XII. The Ring-Opening Polymerization Of Oxetane To Living Polymers Using A Porphinato-Aluminum Catalyst"; *Eur. Polym. J.* vol. 30, No. 5, pp. 641-646, 1994, Elsevier Science Ltd. 1994.

Takeuchi, Daisuke et al.: "Controlled Coordinate Anionic Polymerization of Oxetane by Novel Initiating Systems: Onium Salts/Bulky Organoaluminum Diphenolates"; *Macromolecules 1996*, 29, 8096-8100.

Kanoh, Shigeyoshi et al.: "Cationic Monomer-Isomerization Polymerization of Oxetanes Having an Ester Substituent, to Give Poly(orthoester) or Polyether"; *Macromol. Chem. Phys. 2002*, 203, 511-521; Wiley-Vch.

Kanoh, Shigeyoshi et al.: "Double Isomerization of Oxetane Amides to Azetidine Esters with Ring Expansion and Contraction"; *J. Org. Chem. 2000*, 65, 2253-2256, 2000 American Chemical Society.

Kudo, Hiroto et al.: "Synthesis of a Hetero Telechelic Hyperbranched Polyether. Anionic Ring-Opening Polymerization of 3-Ethyl-3-(hydroxymethyl)oxetane Using Potassium *tert*-Butoxide as an Initiator"; Short Communications; *Polym. J.*, vol. 35, No. 1, 2003; pp. 88-91.

Ueyama, Akihiko et al.: "Preparation of Polyoxetane Resins Having Polyoxirane Segments in the Pendant and Cross-Linking Chains and Uses as Polymeric Solvents for Alkali-Metal Ions"; *Polymer Journal*, vol. 34, No. 12, pp. 944-953 (2002).

Singha, Nikhil K. et al.: "Atom Transfer Radical Copolymerization (ATRCP) Of A Monomer Bearing An Oxetane Group"; *Polymer Preprints 2002*, 43(2), 165.

Sasaki, H. et al.: "The Synthesis, Characterization, And Photoinitiated Cationic Polymerization Of Difunctional Oxetanes"; *J.M.S.-Pure Appl. Chem.*, A29(10), pp. 915-930 (1992).

Ishizone T. et al, "Protection and Polymerization of Functional Monomers". . . Macromolecules, ACS, Washington, DC US, vol. 32, No. 5 Mar. 9, 1999 pp. 1453-1462 XP000804233.

Reiff, helmut et al., Neue 1,3-Propandiole durch nucleophile Ringoffnung von 3-Alkyl-3-hydroxymethyl-oxetanen, Chemical Abstracts Service, Columbus Ohio, US 1973 XP008072234.

* cited by examiner

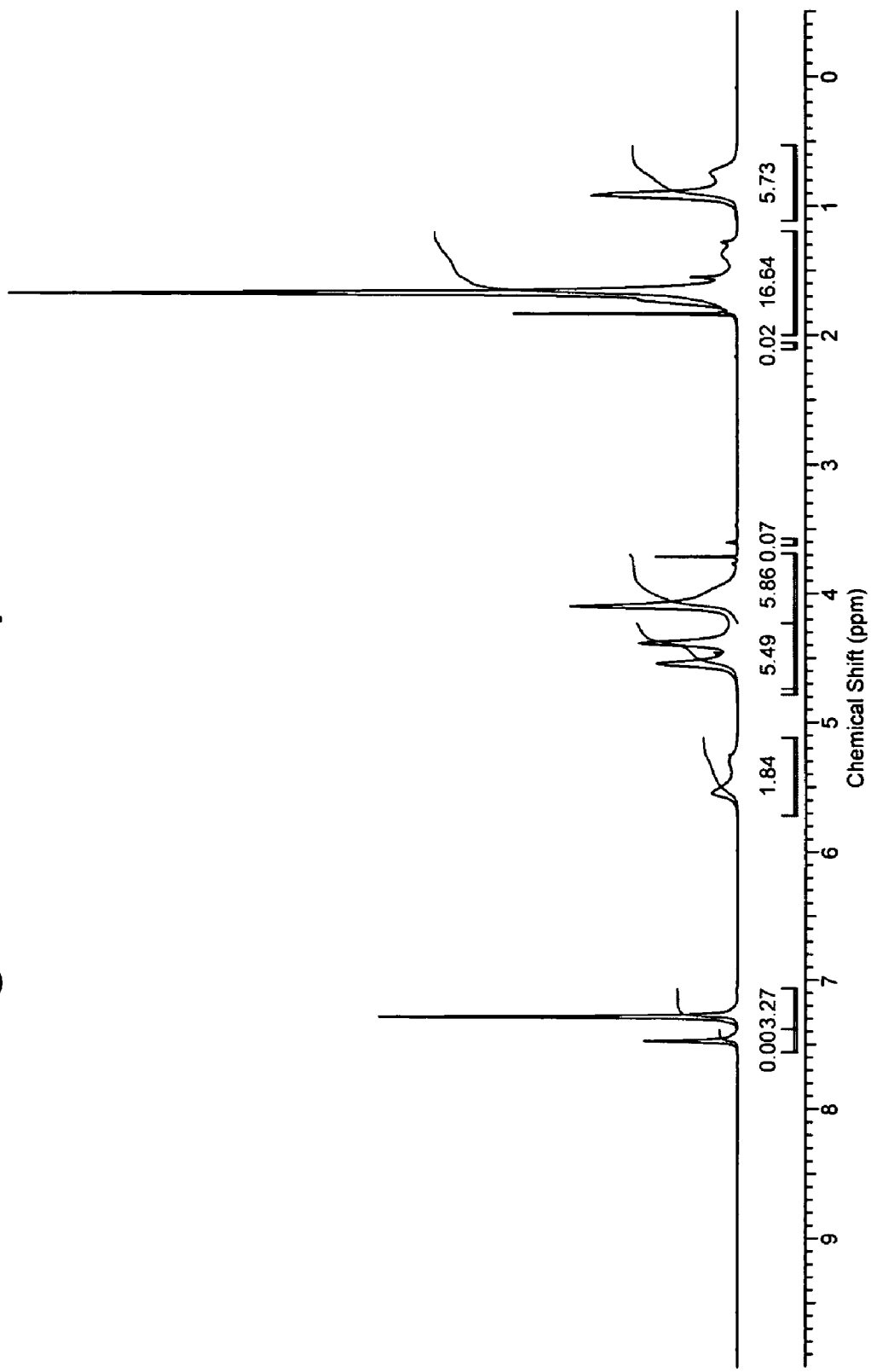

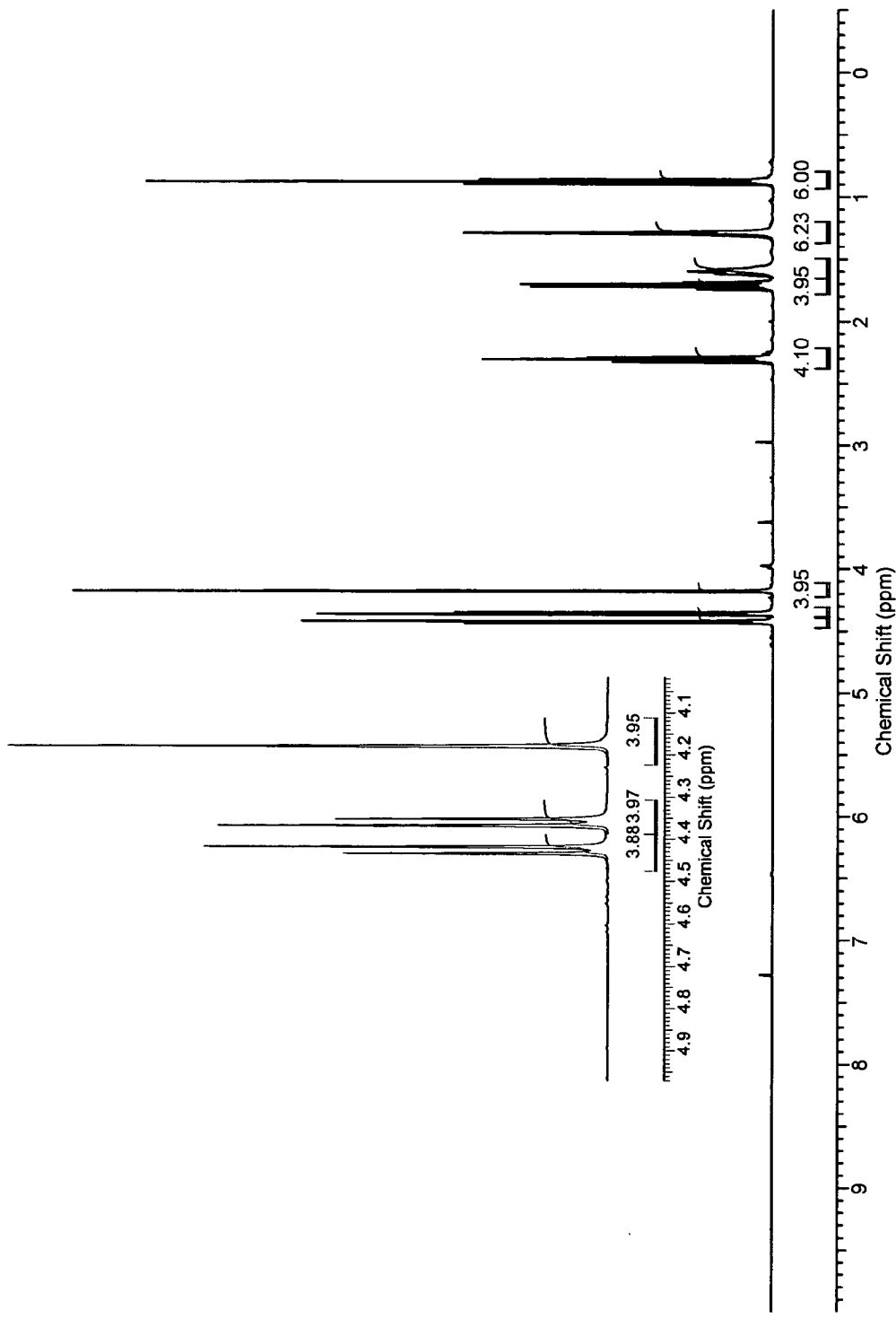
Figure 2. Compound II

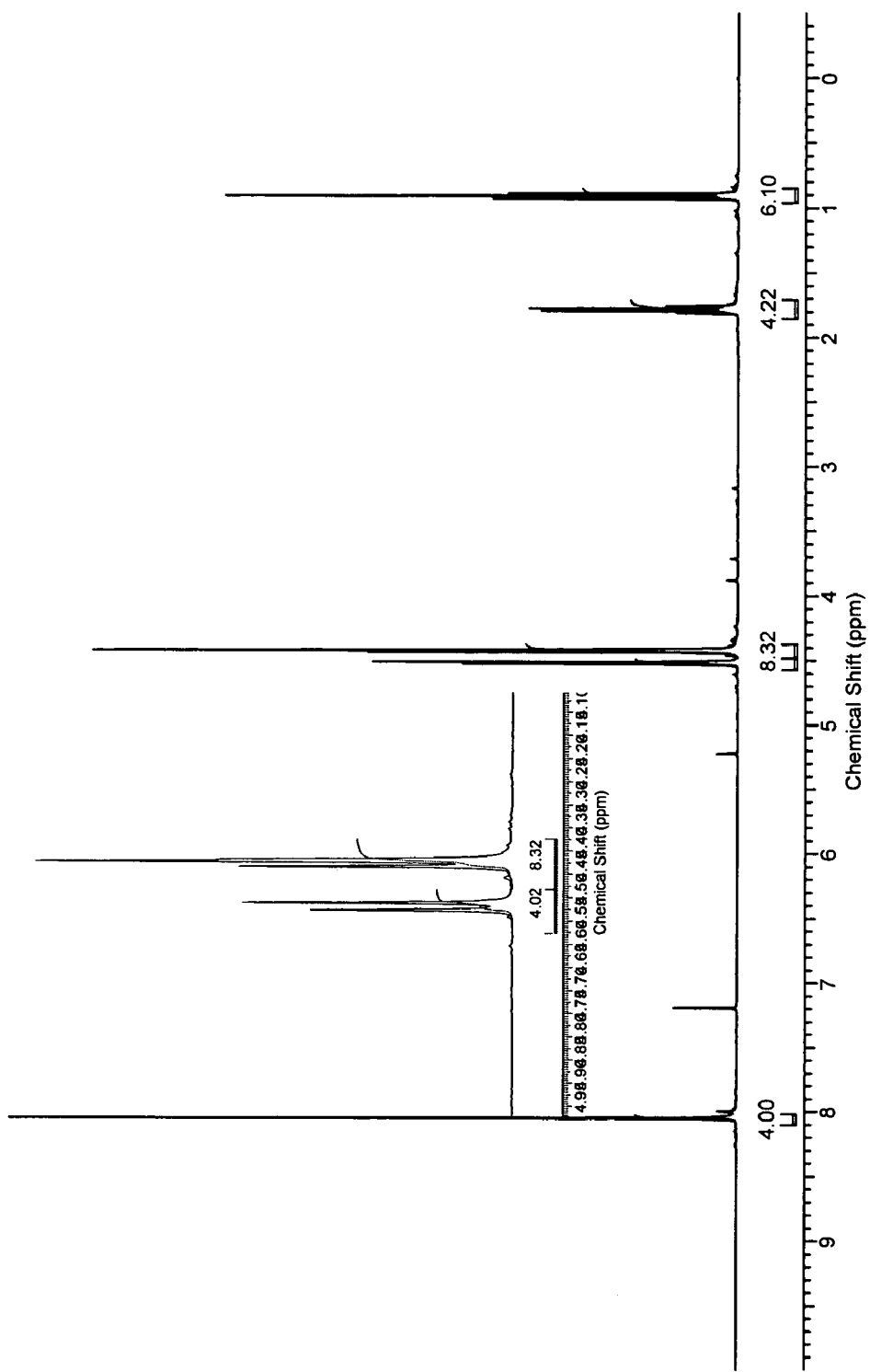
Figure 3: Compound III

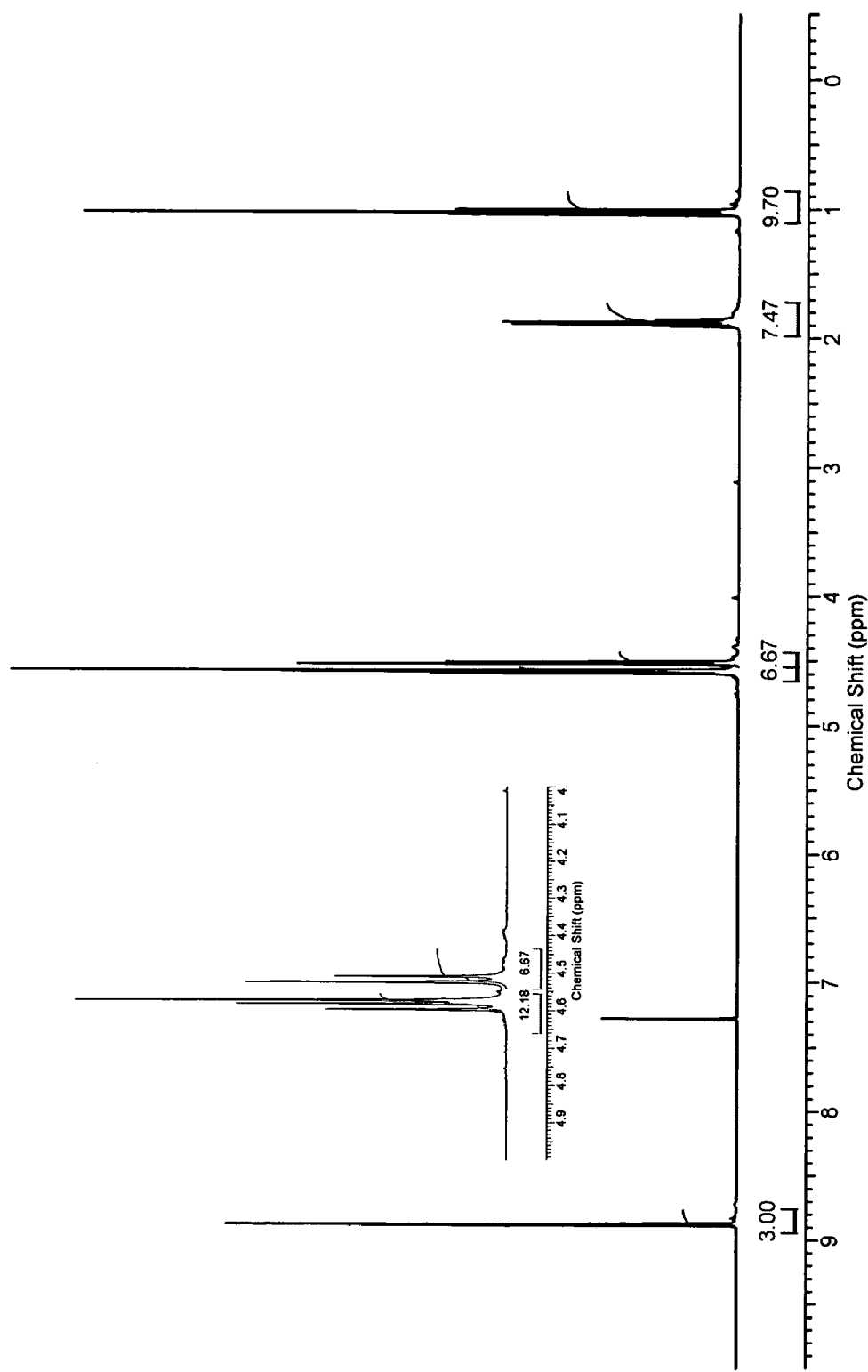
Figure 4: Compound IV

COMPOSITIONS CONTAINING OXETANE COMPOUNDS FOR USE IN SEMICONDUCTOR PACKAGING

FIELD OF THE INVENTION

This invention relates to compositions containing oxetane compounds for use in semiconductor packaging applications, and in particular for use as underfills in assemblies of a semiconductor die attached to a substrate in which the gap between the semiconductor die and substrate is underfilled with a composition containing an oxetane compound.

BACKGROUND OF THE INVENTION

In the manufacture of semiconductors, electrical connections are made between electrical terminals on the semiconductor and corresponding electrical terminals on the substrate for the semiconductor. One method for making these interconnections uses solder or polymeric material that is applied to the terminals. The terminals are aligned and contacted together and the resulting assembly of semiconductor and substrate heated to reflow the solder or polymeric material and solidify the connection. The space between the solder or polymeric connections are filled with a polymeric encapsulant or underfill to reinforce the interconnect and to absorb stress. Two prominent uses for underfill technology are in packages known in the industry as flip-chip, in which a semiconductor chip is attached to a lead frame, and ball grid array, in which a package of one or more chips is attached to a printed wire board.

In some operations the underfill process is designed so that the underfill encapsulant should cure at a higher temperature than that at which the solder or polymeric interconnect material reflows. In the case where the interconnect is lead free, the flow temperature can be as high as 217° C. Thus, the curing temperature of the underfill encapsulant needs to be higher than this temperature. Typical underfill compositions include epoxy, epoxy/phenol, epoxy/anhydride, and cyanate ester systems. These do not always cure at temperatures high enough for the underfill operations using polymeric solder without volatilizing off and, therefore, a need exists for performance materials for high temperature underfill.

BRIEF DESCRIPTION OF THE DRAWINGS

FIG. 1 is the NMR of Compound I.
FIG. 2 is the NMR of Compound II.
FIG. 3 is the NMR of Compound III.
FIG. 4 is the NMR of Compound IV.

SUMMARY OF THE INVENTION

This invention is a composition that is suitable for use as an adhesive or as an underfill encapsulant in the fabrication of electronic devices. The composition comprises an oxetane compound having one or more oxetane rings in which each oxetane ring is one carbon atom removed from an ester, amide, urea, carbamate, carbonate, or carbonyl functionality.

DETAILED DESCRIPTION OF THE INVENTION

Oxetanes are known as highly reactive cyclic ethers that can undergo both cationic and anionic ring opening homopolymerization. In general, oxetanes exhibit low viscosity, shrink minimally upon cure, and polymerize readily. The compounds of this invention, with an appropriate catalyst, have sufficiently high curing temperatures to be suitable for use as underfill encapsulants when lead free interconnect material is used.

The preferred starting material for preparing these oxetane resins is 3-ethyl-3-(hydroxymethyl)oxetane (commercially available as OXT101 from Toagosei), having the structure:

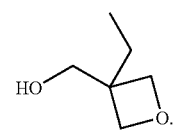

Exemplary resins prepared from 3-ethyl-3-(hydroxymethyl) oxetane and a co-reactive compound include those obtained as follows:

the reaction of 3-ethyl-3-(hydroxymethyl)oxetane with m-tetramethyl-xylene diisocyanate to give the compound

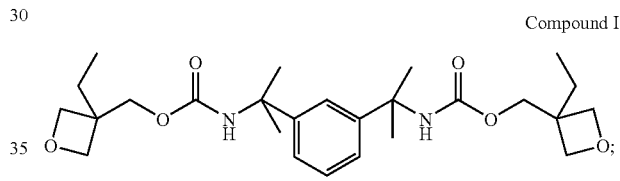

Compound I the reaction of 3-ethyl-3-(hydroxymethyl)oxetane with azelaoyl chloride to give the compound

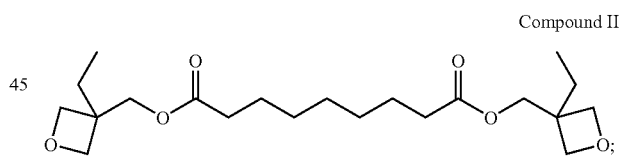

Compound II the reaction of 3-ethyl-3-(hydroxymethyl)oxetane with terephthaloyl chloride to give the compound

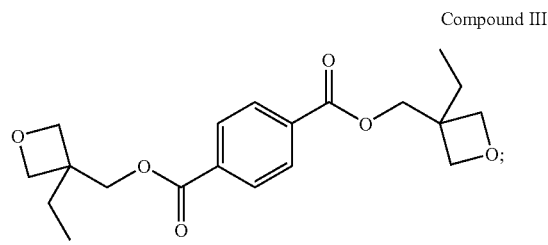

Compound III the reaction of 3-ethyl-3-(hydroxymethyl)oxetane with 1,3,5-benzene-tricarbonyl trichloride to give the compound Compound IV

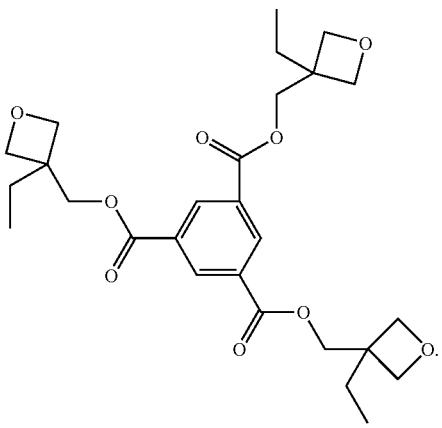

Compounds I, III, and IV are obtained as white solids with melting points of 71° C., 79° C. and 97° C., respectively. Compound II is obtained as a colorless liquid with a viscosity of less than 100 cPs at 25° C. Compounds II, III, and IV contain polar ester linkages, and Compound I contains carbamate functionality, those functionalities being useful for improving adhesion.

Thermogravimetric analysis (TGA) was used to determine the volatility of the above exemplary oxetane resins by heating a sample of each from room temperature to 350° C. at a ramp rate of 10° C./min. The weight loss of each resin was less than 5 wt % at 200° C. This shows that the resins will not volatilize to a detrimental extent before they reach their cure temperature.

Formulations were prepared from these resins and analyzed separately by Differential Scanning Calorimetry to measure kinetic and thermodynamic properties. Compound II was formulated with five weight % of the initiator Rhodorsil 2074 (initiator). Compounds I, II, and III were formulated with a cyanate ester (CE) sold as product AROCY L10 (by Lonza Group) at a 1:1 molar ratio, with and without copper boron acetoacetate (CuBAcAc) as a catalyst, and also formulated with cis-1,2,3,6-tetrahydrophthalic anhydride (THPA) in a 1:1 molar ratio with CuBAcAc as a catalyst.

The L10 cyanate ester has the structure

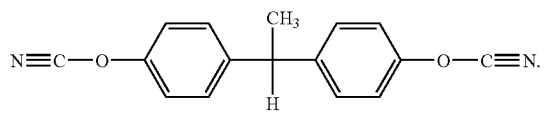

The results are disclosed in Table 1 and show that these resins cure at high temperatures. The results also show that with the proper choice of co-curing material and catalyst, the actual curing temperature of a formulation containing these oxetane materials can be adjusted to suit various curing programs.

TABLE 1

Kinetic and Thermodynamic Properties

| Formulation | (° C.) Curing Temp | (J/g) Heat of Polymerization |
| --- | --- | --- |
| Cmpd II + initiator | 238 | 100 |
| Cmpd I + CE | 258 | 215 |
| Cmpd I + CE + CuBAcAc | 218 | 638 |
| Cmpd I + THPA + CuBAcAc | 241 | 202 |
| Cmpd II + CE | 207 | 415 |
| Cmpd II + CE + CuBAcAc | 195 | 455 |
| Cmpd II + THPA + CuBAcAc | 264 | 223 |
| Cmpd III + CE | 242 | 336 |
| Cmpd III + CE + CuBAcAc | 247 | 412 |
| Cmpd III + THPA + CuBAcAc | 294 | 245 |

In another embodiment, underfill compositions suitable for use in this invention will contain, in addition to the oxetane compound, a cyanate ester compound or resin, a curing initiator, and optionally, a filler. Suitable cyanate ester compounds or resins are commercially available or synthesized by processes known in the art, and can be either aromatic or aliphatic materials. (See, for example U.S. Pat. Nos. 4,785,075 and 4,839,442.) In these embodiments, the cyanate ester will be present in an amount up to 90 weight % of the composition excluding fillers.

In another embodiment, underfill compositions suitable for use in this invention will contain, in addition to the oxetane compound, a curable resin having at least one carbon to carbon double bond, an epoxy, or both. Suitable epoxies are commercially available and can be chosen without undue experimentation by the practitioner. Curable resins having a carbon to carbon double bond include, for example, resins derived from cinnamyl and styrenic starting compounds, fumarates, maleates, acrylates, and maleimides. In these embodiments, the epoxy or the resin containing the carbon to carbon double bond will be present in an amount up to 90 weight % of the composition excluding fillers.

Suitable curing agents include cationic initiators, for example, iodonium, oxonium, sulfonium, sulfoxonium, and various other onium salts. Other suitable cationic initiators include Lewis acid catalysts, such as, copper boron acetoacetate and cobalt boron acetoacetate, and alkylation agents, such as, arylsulfonate esters, e.g., methyl-p-toluenesulfonate and methyl trifluoromethanesulfonate. A preferred series of photoinitiators are those sold under the trademark Irgacure by Ciba Specialty Chemicals or Rhodorsil 2074 by Rhodia. When present, initiators will be present in an amount up to 10 weight % of the formulation.

Suitable fillers can be conductive or nonconductive. Exemplary conductive fillers are carbon black, graphite, gold, silver, copper, platinum, palladium, nickel, aluminum, silicon carbide, boron nitride, diamond, and alumina. Exemplary nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. Fillers generally will be present in amounts of 20% to 90% by weight of the formulation.

These compositions are useful as underfill material between the die and substrate. Typical substrates are fabricated from metal, for example, copper, silver, gold, nickel, alloys (such as, 42Fe/58Ni alloy), silver-coated copper, or palladium-coated copper; from organic material, for example, polyimides, polyamides, or polyesters; from ceramic; and from composites or laminates (such as, printed wire boards)

Various underfill operations are known and used in the art, and the materials disclosed within this specification are suitable for use in those operations. In a typical underfill operation, connections are made between electrical terminals on the die and corresponding electrical terminals on the substrate using metallic or polymeric solder. A bump of solder or lead free polymeric solder is placed on the terminals of the substrate, the terminals are aligned and contacted, and the resulting assembly heated to reflow the solder. A gap is created between the die and the substrate, which is filled with the underfill encapsulant to reinforce the interconnect.

There are variations in the processes for the underfill, which variations are known to those skilled in the art. For example, the underfill material can be placed along the periphery of the gap between the die and substrate and enter and fill the cap by capillary action. In another process, the underfill can be applied to the silicon wafer before it is diced into individual dies. Curing of the underfill material may take place after the reflow of the solder or simultaneously with the reflow of the solder, depending on the curing temperature of the underfill material and the process chosen.

SYNTHETIC EXAMPLES

Synthesis of Compound I

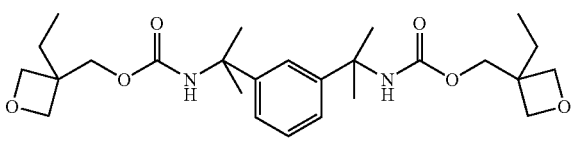

A 500 mL flask was charged with m-tetramethylxylene diisocyanate (24.43 g, 0.1 mol). The reaction vessel was placed under $N_2$ blanket and equipped with an overhead stirrer and condenser. Two drops of dibutyl tin dilaurate were charged to the mixture and the mixture was heated to 60° C. 3-Ethyl-3-(hydroxymethyl)oxetane (23.20 g, 0.2 mol) was placed in the addition funnel. Stirring was continued and the temperature was kept at 60° C. by dropwise exothermic addition from the addition funnel over a period of 20 minutes. The reaction was monitored by FT-IR analysis for the consumption of isocyanate (peak at 2258 $cm^{-1}$). The reaction was completed after four hours. After this interval, the reaction mixture was dissolved into dichloromethane (150 mL). Silica gel (50 g) was added. The organics were filtered and the solvent was removed in vacuo (60° C., 0.3 mm Hg) to afford a white solid with a melting point of 71° C. The NMR for this compound is shown in FIG. 1.

Synthesis of Compound II

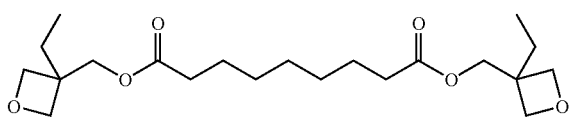

The initial charge was added to a 500-mL 4-neck round bottom flask: 3-ethyl-3-(hydroxymethyl)oxetane (25.76 g, 0.222 mol), triethylamine (22.464 g, 0.222 mol), dimethylaminopyridine (2.712 g, 0.022 mol) and dichloromethane (180 mL). The reaction vessel was equipped with an overhead mixer and condenser. Stirring was continued until the mixture became homogeneous. The temperature was kept between 0° and 10° C. Azelaoyl chloride (25 g, 0.111 mol) was charged dropwise to the flask over a period of one hour. The reaction was monitored by FT-IR analysis for the consumption of carbonyl group in acid chloride (peak at 1801 $cm^{-1}$) and the formation of ester group in product (peak at 1736 $cm^{-1}$). The reaction was completed after 24 hours. The reaction mixture was washed with water (5×50 mL). The organics were dried over $MgSO_4$, filtered, and the solvent was evaporated off at bath temperature of 50° C. Product was then dissolved in 50/50 hexane and ethyl acetate mixture (250 mL) and silica gel (8 g) was added. Silica gel was filtered out and the solvent was removed in vacuo (60° C., 0.3 mm Hg) to afford a clear yellow liquid (31 g, 0.081 mol, 67%) with a viscosity of less than 100 mPa·s at room temperature. The NMR for this compound is shown in FIG. 2.

Synthesis for Compound III

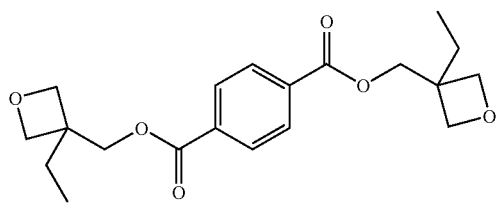

The initial charge was added to a 500-mL 4-neck round bottom flask: 3-ethyl-3-(hydroxymethyl)oxetane (40 g, 0.344 mol), triethylamine (34.809 g, 0.344 mol), dimethylaminopyridine (4.203 g, 0.034 mol) and dichloromethane (300 mL). The reaction vessel was equipped with an overhead mixer and condenser. Stirring was continued until the mixture became homogeneous. The temperature was kept between 0° and 10° C. Terephthaloyl chloride (35.0 g, 0.172 mol) was dissolved into dichloromethane (100 mL) and the mixture was charged to the flask by dropwise addition over a period of one hour. The reaction was monitored by FT-IR analysis for the consumption of carbonyl group in acid chloride (peak at 1801 $cm^{-1}$) and the formation of ester group in product (peak at 1736 $cm^{-1}$). The reaction was completed after 24 hours. The reaction mixture was washed with water (5×50 mL). The organics were dried over $MgSO_4$, filtered, and the solvent was evaporated off at bath temperature of 50° C. Product was mixed with ethyl acetate (300 mL) and the temperature was reduced below −30° C. by dry ice. An insoluble white solid (product) precipitated out. Product was filtered and washed with hexane (3×30 mL) to afford a white solid with a melting point of 79° C. The NMR for this compound is shown in FIG. 3.

Synthesis of Compound IV

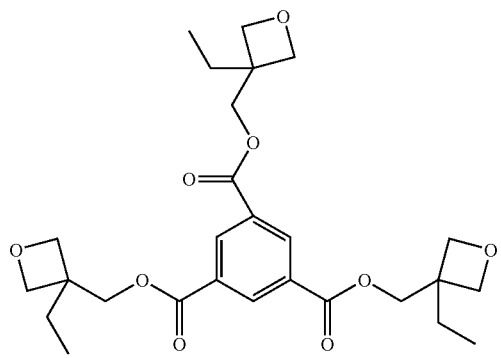

The initial charge was added to a 500-mL 4-neck round bottom flask: 3-ethyl-3-(hydroxymethyl)oxetane (40 g, 0.344 mol), triethylamine (34.809 g, 0.344 mol), dimethylaminopyridine (4.203 g, 0.034 mol) and dichloromethane (300 mL). The reaction vessel was equipped with an overhead mixer and condenser. Stirring was continued until the mixture became homogeneous. The temperature was kept between 0° and 10° C. 1,3,5-Benzenetricarbonyl trichloride (30.442 g, 0.115 mol) was dissolved into dichloromethane (100 mL) and the mixture was charged to the flask dropwise over a period of one hour. The reaction was monitored by FT-IR analysis for the consumption of carbonyl group in acid chloride (peak at 1801 cm$^{-1}$) and the formation of ester group in product (peak at 1736 cm$^{-1}$). The reaction was completed after 24 hours. The reaction mixture was washed with water (5×50 mL). The organics were dried over MgSO$_4$, filtered, and the solvent was evaporated off at bath temperature of 50° C. Product was mixed with ethyl acetate (300 mL) and temperature was reduced below −30° C. by dry ice. An insoluble white solid (product) precipitated out. Product was filtered and washed with hexane (3×30 mL) to afford a white solid with a melting point of 97° C. The NMR for this compound is shown in FIG. 4.

What is claimed is:

1. A curable composition comprising an oxetane compound selected from the group consisting of

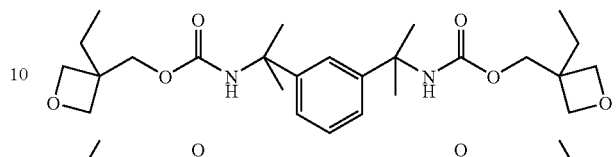

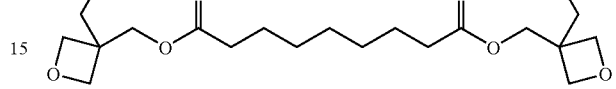

and

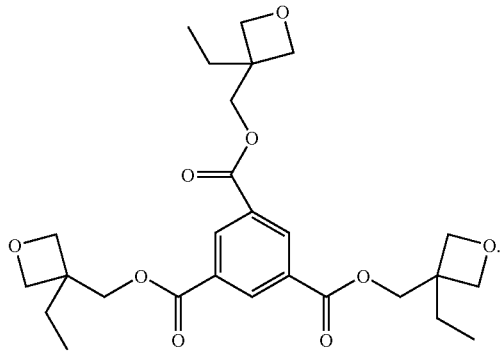

2. The curable composition according to claim 1 further comprising a cyanate ester compound.

3. The curable composition according to claim 1 further comprising an epoxy, a resin having a carbon to carbon double bond, or both.

* * * * *